(12) United States Patent
Abels et al.

(10) Patent No.: US 6,491,715 B1
(45) Date of Patent: Dec. 10, 2002

(54) DEVICE FOR TREATING GROWING, DILATED OR MALFORMED BLOOD VESSELS AND METHOD FOR TREATING BIOLOGICAL MATERIAL

(75) Inventors: Christoph Abels, Regensburg (DE); Rolf-Markus Szeimies, Zeitlarn (DE)

(73) Assignee: Pulsion Medical Systems AG, Munich (DE)

(*) Notice: Subject to any disclaimer, the term of this patent is extended or adjusted under 35 U.S.C. 154(b) by 0 days.

(21) Appl. No.: 09/532,815

(22) Filed: Mar. 21, 2000

(30) Foreign Application Priority Data

Nov. 17, 1999 (DE) .......................................... 199 54 710

(51) Int. Cl.[7] .............................................. A61N 5/006
(52) U.S. Cl. ................................ 607/89; 607/88; 606/3; 606/7; 606/10; 606/11; 606/12; 128/898; 604/21; 604/27; 604/48
(58) Field of Search ................... 606/3, 7–12; 128/898; 604/19–48, 500–508

(56) References Cited

U.S. PATENT DOCUMENTS

| | | | | |
|---|---|---|---|---|
| 4,305,390 A | | 12/1981 | Schwartz | 128/207 |
| 4,592,361 A | | 6/1986 | Stanbro et al. | 128/633 |
| 5,002,054 A | * | 3/1991 | Ash et al. | 128/635 |
| 5,071,417 A | | 12/1991 | Sinofsky | |
| 5,104,392 A | * | 4/1992 | Kittrell et al. | 606/15 |
| 5,193,545 A | * | 3/1993 | Marsoner et al. | 128/635 |
| 5,207,670 A | * | 5/1993 | Sinofsky | 606/8 |
| 5,237,993 A | * | 8/1993 | Skrabal | 128/632 |
| 5,304,170 A | | 4/1994 | Green | |
| 5,394,199 A | | 2/1995 | Flower | |
| 5,483,958 A | * | 1/1996 | Merberg et al. | 128/634 |
| 5,520,680 A | * | 5/1996 | Shapshay et al. | 606/12 |
| 5,572,996 A | * | 11/1996 | Doiron et al. | 128/633 |
| 6,132,423 A | * | 10/2000 | Aita et al. | 606/7 |
| 6,162,213 A | * | 12/2000 | Stewart | 606/10 |
| 6,240,925 B1 | * | 6/2001 | McMillan et al. | 128/898 |
| 6,391,049 B1 | * | 5/2002 | McNally et al. | 606/214 |
| 6,428,531 B1 | * | 8/2002 | Visuri et al. | 606/7 |
| 6,428,532 B1 | * | 8/2002 | Doukas et al. | 606/9 |

FOREIGN PATENT DOCUMENTS

| | | |
|---|---|---|
| DE | 43 13 011 A | 10/1994 |
| WO | WO 91/18646 | 12/1991 |
| WO | WO 93/03793 | 3/1993 |
| WO | WO 97/31582 | 9/1997 |

OTHER PUBLICATIONS

Elias Reichel, M.D., et al., :Indocyanine Green Dye–Enhanced Diode Laser Photocoagulation of Poorly Defined Subfoveal Choroidal Neovascularization, Ophthalmic Surgery, Mar. 1994, vol. 25, No. 3, pp. 195–201.

* cited by examiner

Primary Examiner—Linda C. M. Dvorak
Assistant Examiner—Ahmed Farah
(74) Attorney, Agent, or Firm—Squire, Sanders & Dempsey, L.L.P.

(57) ABSTRACT

In a device for treating blood vessels with a laser, the laser provides a beam in a wavelength range from 750 to 850 nm, preferably 805 nm. The device has a measuring unit which measures the concentration of a chromophore (preferably indocyanine green) administered to the patient in the patient's blood vessels. The device further comprises a control unit which controls the power of the laser in a contrary sense to the measured concentration.

40 Claims, 3 Drawing Sheets

DEVICE FOR TREATING GROWING, DILATED OR MALFORMED BLOOD VESSELS AND METHOD FOR TREATING BIOLOGICAL MATERIAL

BACKGROUND OF THE INVENTION

1. Field of the Invention

Description

The invention relates to a device for treating growing, dilated or malformed blood vessels with a laser which emits radiation in a wavelength range from 750 nm to 850 nm.

2. Description of the Related Art

WO 97/31582 has already disclosed the treatment of, for example, tumors by administering to the patient a dye or chromophore having an absorption maximum in a wavelength range from 770 nm to 840 nm, and treating the diseased area of the body with light having a wavelength in the stated range. Indocyanine green is proposed as dye or chromophore. A diode laser is a preferred light source.

U.S. Pat. No. 5,394,199 discloses the production of angiographic images of the capillary network of the eye (choriocapillaris) using indocyanine green in order to use them for precise adjustment of the therapeutic laser.

"Ophthalmic Surgery", March 1994, Vol. 25, No. 3, pages 195–201 discloses the selective removal of choroidal neovascular membranes with administration of ICG and treatment with a diode laser having an emission wavelength of 805 nm.

U.S. Pat. No. 5,304,170 discloses the destruction of carotene-containing body tissue with a laser with an emission wavelength of 504 nm. It is provided for this purpose to increase the carotene content by administering carotene.

U.S. Pat. No. 5,071,417 discloses an apparatus for fusion of biological material using a laser. Since the progress of such a fusion is often difficult to observe with the naked eye, the apparatus is equipped with a reflectance monitor which establishes the change in the reflectance characteristics of the tissue material caused by the fusion and thus indicates the success of the fusion to the therapist.

WO 91/18646 discloses a device for laser photothermotherapy. In the disclosed device, tissue which contains endogenous or exogenous chromophore is irradiated with a laser. The temperature of the treated tissue is measured, and the measured signal is used to control the pulse energy and the rate of repetition of the laser pulses.

WO 93/03793 discloses a medical light treatment apparatus, in particular for acupuncture. With the apparatus, the light reflected by the biological tissue is detected and, on the basis of this detection, the energy of the light directed into the tissue is controlled.

In summary, concerning the prior art discussed above it can be stated that most known devices are not intended and not suitable for treating blood vessels, in particular for treating small blood vessels (spider veins). The known devices chiefly make use of endogenous chromophores such as, for example, hemoglobin for absorbing the laser light. The problem which therefore arises on treatment of blood vessels is that vessels which are too small contain too little hemoglobin whereas blood vessels which are too large cannot, because of the poor absorption properties of hemoglobin and the increased heat convection, be heated sufficiently and thus in both cases a sufficient thermal effect with subsequent coagulation of the vessel is not achieved.

SUMMARY OF THE INVENTION

The invention is by contrast based on the object of providing a device for treating growing, dilated or malformed blood vessels with a laser, which is distinguished in that the blood vessels are effectively coagulated and adverse effects on the surrounding tissue are minimal. It is further object of this invention to provide a method for treating biological material with a light beam.

These objects are achieved according to the invention with a device and a method for treating growing, dilated or malformed blood vessels with a laser which emits radiation in a wavelength range from 750 nm to 850 nm and which has a measuring unit which measures the concentration of an exogenous chromophore which absorbs the laser beam in a blood vessel to be treated, and which also has a control unit which controls the power of the laser in a contrary sense to the measured concentration. The measurement according to the invention of the concentration of an exogenous chromophore, i.e. chromophone which has been administered to the patient, and the corresponding control of the laser power makes it possible to meter the laser power optimally. As long as the concentration of the exogenous chromophore in the blood vessel to be treated is high, a lower laser power is sufficient. If over the course of time, as a consequence of the breakdown or excretion of the exogenous chromophore from the blood circulation, the concentration thereof falls, in the device according to the invention the power of the laser is controlled in the contrary sense, i.e. increased. It may be pointed out in this connection that power means the energy per unit time (with watt as unit of measurement) introduced into the vessel by the treatment.

The concentration of the exogenous chromophore in the blood vessel can be measured in a variety of ways, for example also by taking a blood sample.

However, a particularly advantageous measuring unit is designed as a reflection measuring unit because this operates non-invasively and is accordingly associated with less stress for the patient. A certain fraction of the laser light which impinges on the surface of the skin is, owing to the different refractive indices of air and skin, reflected (reflection coefficient R).

$$P_1 \text{ is } P_0 - RP_0 = P_0(1-R)$$

where $P_1$ is the reflected and $P_0$ is the originally emitted power. The fraction $P_2$ of the original power $P_0$ which arrives, after passing through the epidermis and part of the dermis, at the blood vessel emerges from the following formula:

$$P_2 = P_1 \exp(-\alpha_{mel}(\lambda)z) - P_1 R_H = P_1[\exp(-\alpha_{Mel}(\lambda)z) - R_H]$$

$$P_2 = P_0(1-R)[\exp(-\alpha_{MEL}(\lambda)z) - R_H)].$$

In this, the factor $\alpha_H(\lambda)z$ describes the attenuation of the laser light in the direction of propagation z from the surface of the skin until the particular blood vessel is reached. The factor $\alpha_{Mel}(\lambda)z$ depends on the melanin content of the particular section of skin. The absorption, mediated by the chromophore concentration, of the laser light of power P is thus $$P = P_2(1-T)$$

$$P = P_0(1-R)[\exp(-\alpha_{Mel}(\lambda)z) - R_H][1-\exp(-\alpha_{CH}((\lambda,t)z)]$$

The attenuation of the laser light by the reflection R, the internal reflection $R_H$ and by the factor $\exp(-\alpha_{Mel}(\lambda)z)$ does not, in contrast to the chromophore concentration $\alpha_{CH}(\lambda,t)$, vary with time. It is possible by measuring the reflected proportion of the incident light to determine, by the above calculation, the changing chromophore concentration in the blood vessel ($\alpha_{CH}((\lambda,t))$. The control unit controls, on the basis of the measured chromophore concentration, the power of the laser in the contrary sense to the measured concentration, i.e. the power of the laser is set at a comparatively low level when the concentration is high, whereas a comparatively high laser power is applied when the concentration is relatively low.

Another advantageous embodiment of the invention provides for the control unit, in order to measure the concentration of the chromophore, to cause a pilot light pulse to be emitted, the power of which is so small that it causes no permanent changes in the blood vessel or the tissue surrounding the latter. There is merely determination of the chromophore concentration on the basis of the pilot light pulse, so that this concentration can be set appropriately beforehand, i.e before starting the treatment. The control unit can moreover be programed so that such a pilot light pulse can be emitted at regular intervals or, for example, before emitting each therapeutic pulse, in order to detect changes in the chromophore concentration in good time.

A computer unit then determines the chromophore concentration from a power of the pilot light pulse and the reflected light power, measured by the measuring unit, using the formula indicated above.

It may also be provided in one embodiment for the measuring unit to use its own measuring light source. The light from the measuring light source can be directed onto the therapy area, but with this embodiment there is also the possibility of directing the light from the measuring light source onto another body area on which the chromophore concentration in the patient's blood can easily be measured.

It has proven advantageous in the control of the laser power for the latter to be controlled in inverse proportion to the chromophore concentration found. The product of the applied laser power and measured concentration therefore remains essentially constant during the treatment. The laser beam is preferably emitted in the form of pulses, preferably in the form of rectangular pulses with a duration not exceeding 10 ms, preferably with a duration of from 1 to 5 ms. The use of such short light pulses in conjunction with a relatively high power ensures that the therapeutic light can penetrate into the vessel and pass through the vessel, and the coagulation process induced by the heat is restricted to the vessel. In some applications, however, it has also proven advantageous to control the laser so that the pulses can be executed not as single pulses but as double pulses with a pause of less than 5 ms. A pause of less than 5 ms is below the thermal relaxation time so that the therapeutic effect of the second pulse is also still ensured. On the other hand, however, the pause allows interim cooling of the surrounding tissue, especially of the tissue located in front of the blood vessel, so that this mode of operating the laser has proven to be harmless to tissue.

In another advantageous embodiment of the invention, the control unit is designed so that the pulse length is controlled in a contrary sense to the power. This is because it has proven advantageous for vessel treatment if the pulse length is increased, for example if the power of the laser beam is reduced because of a high chromophore content, so that the total energy of a light pulse introduced into the vessel is kept approximately constant The laser advantageously used is a diode laser with a power of from 100 to 800 watts and an emission wavelength of 805 nm.

In order to guide the laser light with great accuracy onto the patient's vessels to be treated, an advantageous embodiment provides for the laser to be connected via a light guide to a handpiece. The hand-piece can have a transparent contact area for contact with the patient's skin. It is also possible to provide in the handpiece, similar to a dermatoscope, an illumination unit and a magnifier, and a scale for measuring the vessels to be treated. The laser beam is guided into the dermatoscope-like handpiece by a spectrally selective mirror, preferably a dichroic mirror, it being possible for the therapist to observe the therapy area through the mirror from behind it. The therapist is able by means of an aiming mark, which is preferably attached on the transparent contact area, in the handpiece, to direct the laser beam specifically onto the vessel to be treated. The therapist is able to establish the size of the vessel by a scale in the handpiece.

An advantageous embodiment of the invention provides in the handpiece an adjustable aperture with which the diameter of the laser beam can be limited so that only the vessel is irradiated and irradiation of tissue beyond the margins of the vessel is avoided.

A particularly advantageous embodiment provides for the control unit to block emission of laser light by the laser when the chromophore concentration found by the measuring unit is below a preset lower threshold. Below a particular lower threshold of chromophore concentration it would be necessary for the power of the laser to be high to compensate for this low concentration, which would not be optimal for the therapy. The blocking of the device therefore avoids such inappropriate treatment in the region where the chromophore concentrations are too low.

Surprisingly, it has also emerged that a treatment may be insufficient if the chromophore concentrations are too high. A further advantageous embodiment of the invention therefore provides for the control unit to block emission of light pulses by the laser when the chromophore concentration found by the measuring unit is above a preset upper threshold. This is because it has been found that when the chromophore concentrations are too high the therapeutic laser light is absorbed so strongly that it is unable to penetrate sufficiently through the vessel to be treated. On the contrary, the laser light is absorbed exclusively on the margin of the vessel so that the coagulation does not extend over the complete vessel cross section, and the vessel thus cannot be sclerosed as desired.

A further advantageous embodiment of the invention provides an intensity sensor, which is preferably accommodated in the handpiece. The intensity sensor is able to measure the light reflected at the treatment site in order to determine the exogenous chromophore concentration. However, it is also possible, instead of accommodating the intensity sensor in the handpiece, to arrange an outcoupling mirror in the laser light path to pass reflected light to the intensity sensor. In this case, the intensity sensor can advantageously be arranged near the laser.

An advantageous embodiment is also one in which the handpiece is connected to a video camera. The therapy area can be displayed by the video camera on a monitor, in which case a false color display of the chromophore concentration facilitates the finding by the therapist of the blood vessels to be treated. In a further advantageous embodiment of the invention, the handpiece is provided with a cooling unit, preferably a Peltier element. This can remove the heat which is released during the treatment and frequently felt to be unpleasant by the patient.

Other features, characteristics and advantages of the present invention will become apparent from the following description of the invention, which refers to the accompanying drawings:

DETAILED DESCRIPTION OF THE PREFERRED EMBODIMENTS

Figure 1:
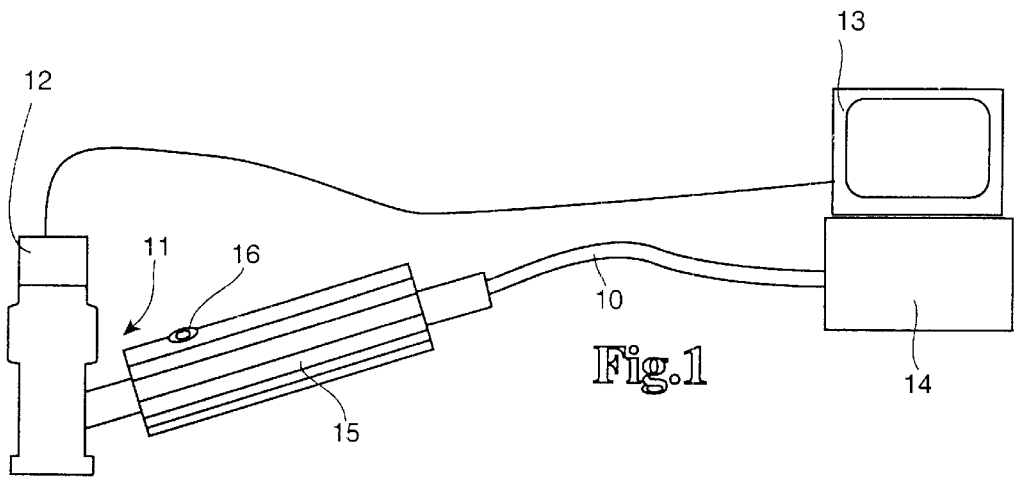
FIG. 1 a device for treating blood vessels according to the invention.

The principal parts of the laser treatment device according to the invention are evident in FIG. 1. These are the dermatoscope-like handpiece 11 with handle 15 which is connected via a light guide 10 to a central unit 14. A trigger switch 16 is present on the handle 15 and can be used by the therapist to activate the laser. As will be explained in detail hereinafter, the central unit 14 contains the laser, the control unit belonging thereto and the measuring unit provided for measuring the exogenous chromophore concentration. A video camera 12 is coupled to the handpiece 11 and is connected to a monitor 13.

Figure 2:
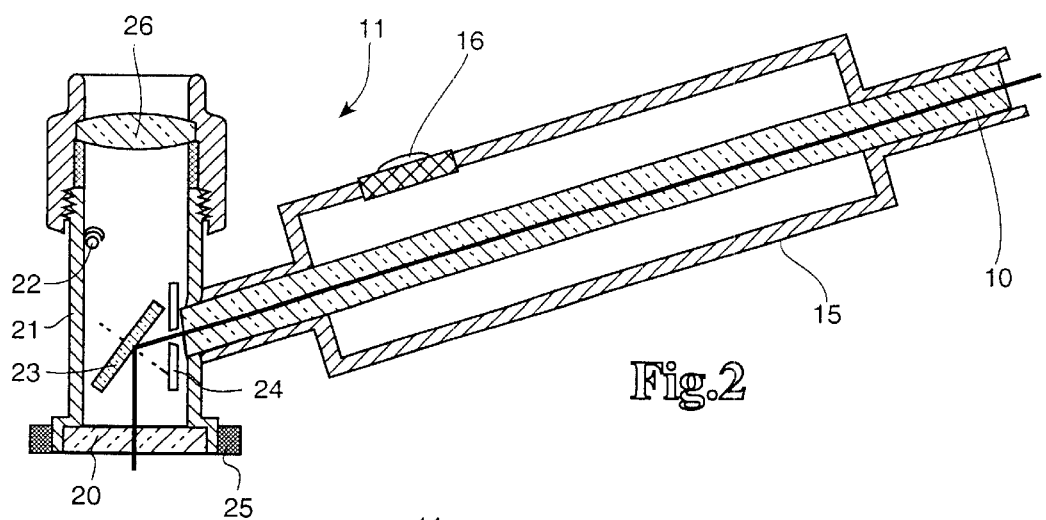
FIG. 2 the handpiece used with the device shown in FIG. 1, depicted in section on an enlarged scale.

As is evident from FIG. 2, the handpiece has a cylindrical housing 21 with a magnifying lens 26. Inside the housing 21 there is an incandescent lamp 22 whose current supply wires (not depicted) pass through the handle 15 to the central unit 14. The cylindrical housing 21 is terminated at its end opposite the magnifier 26 by a flat glass plate. A light guide 10 projects into the housing through a lateral opening in the housing 21 and passes through the handle 15 which has already been mentioned. A dichroic mirror 23 is arranged opposite the light guide, which projects slightly into the housing 21, and is inclined so that the laser beam emerging from the light guide 10 is directed perpendicularly onto the glass plate 20. The housing 21 is encircled in the region of the glass plate 20 by a Peltier element 25 which cools the glass plate. The diameter of the laser beam can be limited as required by an adjustable aperture 24 which is arranged opposite the end of the light guide 10.

The depiction of the handpiece as shown in FIG. 2 omits the video camera shown in FIG. 1. The therapist is therefore able to look through the magnifier 26, through the dichroic mirror 23 and the glass plate 20 onto the therapy field which is illuminated by the lamp 22. The dichroic mirror is adjusted for this purpose so that it reflects only the laser light (805 nm), whereas it transmits the remaining spectral region, in particular the visible spectral region, and thus does not interfere with observation of the therapy area.

Figure 3:
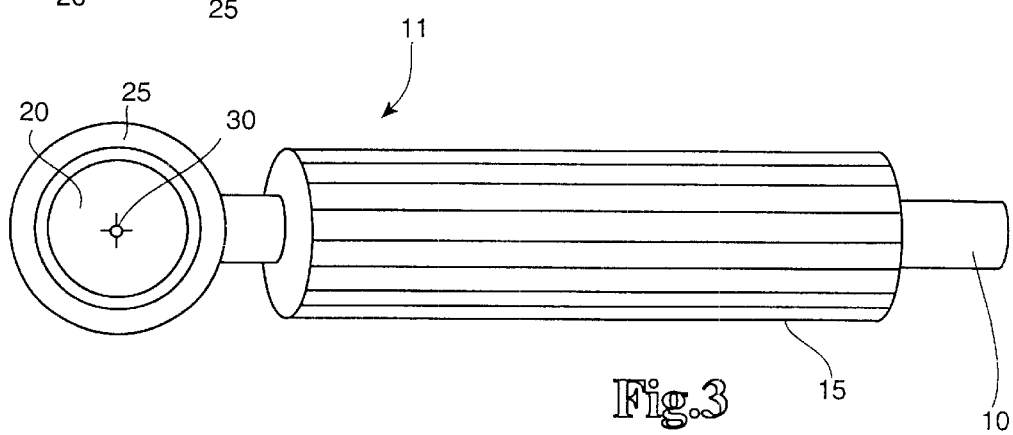
FIG. 3 the handpiece shown in FIG. 2 viewed from below.

As is evident from the depiction of the handpiece from underneath shown in FIG. 3, the glass plate 20 is provided with an aiming mark 30 which can be used for precise aiming at the vessel to be treated before the laser pulse is triggered.

Figure 4:
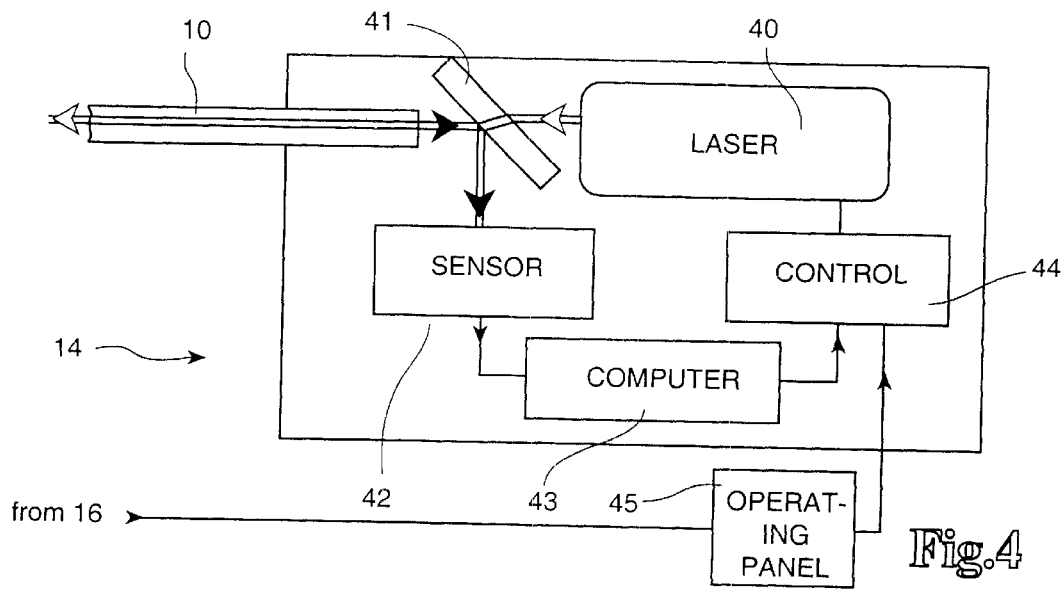
FIG. 4 the central unit used with the device shown in FIG. 1, with laser, control and measuring unit.

FIG. 4 shows a schematic circuit diagram of the central unit 14. The central unit comprises a diode laser 40 (wavelength 805 nm) which is controlled by a control unit 44. A light intensity sensor 42 is also provided, and its output signal is passed to a computer 43. The output of the computer 43 is connected to the input of the control system 44. The light emerging from the laser 40 passes through an inclined mirror 41 and is fed into the light guide 10, through which it is passed to the handpiece.

Light reflected from the therapy area passes from the handpiece 11 (FIG. 2) in the light guide 10 back to the central unit 14. Part of the light is reflected there at the inclined mirror 41 and reaches the intensity sensor which provides an electrical signal which corresponds to the power of the reflected signal.

The device described in this way operates as follows:

For example for removing visible veins on the leg (so-called spider veins), a patient receives intravenous administration of indocyanine green (as chromophore) in a dose of 1–10 mg per kg of body weight. Before the administration, a laser pulse of low power is emitted onto the skin area to be treated in order to determine in a type of blank test the reflection properties of the skin area (Mel, RH). This is done by switching the control system via an operating panel 45 to the "calibration" operating state. The corresponding values are stored in the computer 43. As soon as the indocyanine green (ICG) is uniformly distributed in the vascular system, the control system is switched via the operating panel 45 to the "therapy" operating state, and a laser pulse of low energy is again emitted, and the therapist before activating the trigger switch 16 adjusts the handpiece using the aiming device 30 so that the laser beam impinges on a vessel to be treated. The reflection which occurs is determined again via the outcoupling mirror 41 and the intensity sensor 42, and the computer 43 calculates the concentration of the indocyanine green from the comparison with the previously described blank test. The computer 43 also calculates the laser power appropriate for the concentration and transmits the value to the control unit 44. Immediately thereafter, a laser pulse lasting about 2 ms with an appropriate energy in the range from 100 to 800 watts (depending on the measured concentration) is emitted. The light power is such that the light is absorbed predominantly in the blood vessel to be sclerosed and is converted into heat there, so that the blood coagulates and the vessel is destroyed at the irradiated point. If the ICG concentration in the patient's blood becomes too high or if it is too low, this is detected by the computer and indicated by a warning light (not depicted). At the same time, emission of the pulse is blocked so as to ensure that the treatment takes place only in the correct ICG concentration range.

Figure 5:
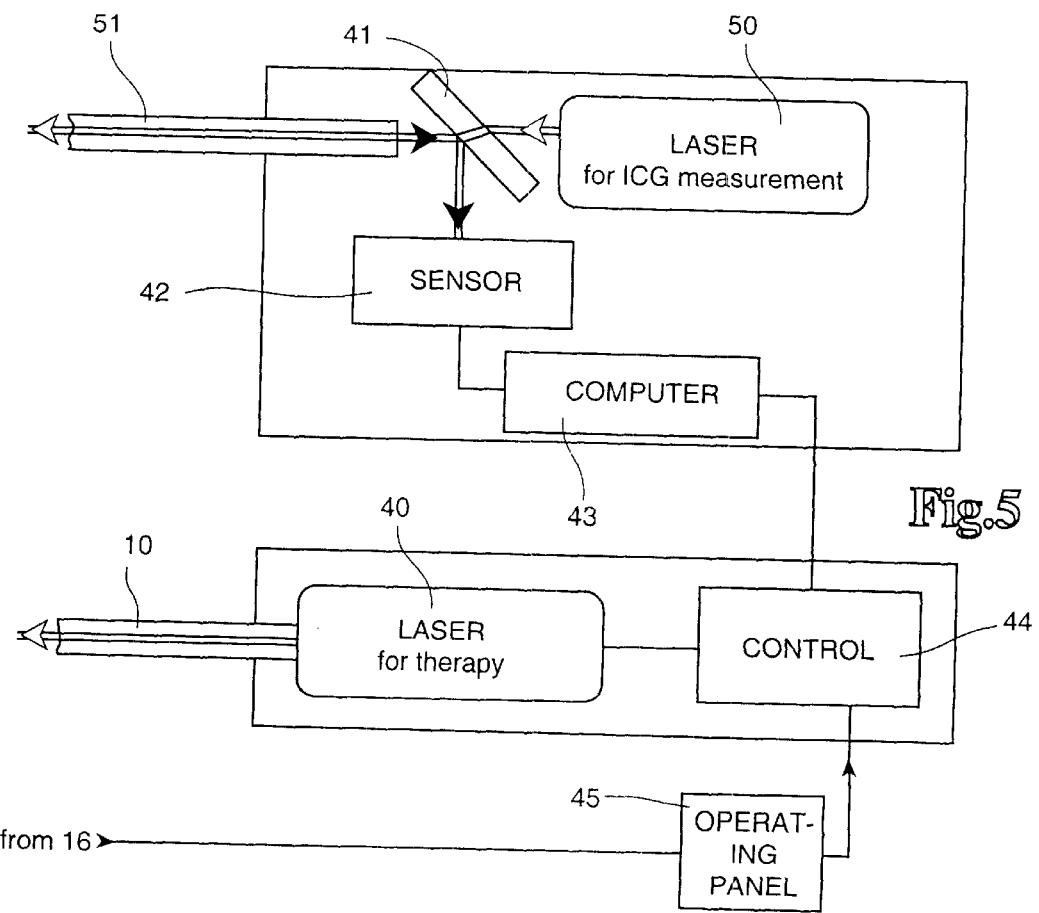
FIG. 5 one embodiment of the central unit.

FIG. 5 shows one embodiment of the central unit. The central unit shown in the embodiment of FIG. 1 has, in addition to a separate laser 40 for therapy and the control system 44 belonging thereto, another laser 50 which is provided only for determining the ICG concentration. The laser light is fed into an additional light guide 51, and the proportion of the light reflected in the therapy area is passed back through the light guide 51 to the central unit where it is passed via the outcoupling mirror 41 to the sensor 42. The signal from the intensity sensor 42 is in turn passed to the computer 43 which in a manner analogous to that described above calculates the laser power and optionally also the pulse duration and transmits appropriate signals to the control system 44. The central unit shown in FIG. 5 allows measuring the ICG concentration in the blood vessels continuously at any site on the body, without emitting test light pulses.

Figure 6:
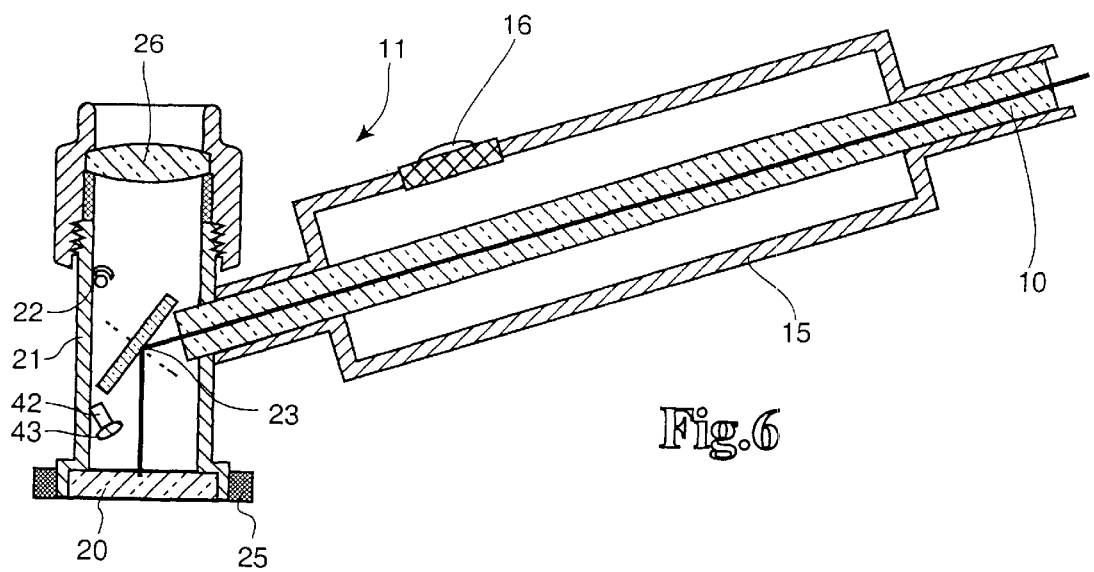
FIG. 6 one embodiment of the handpiece.
Figure 7:
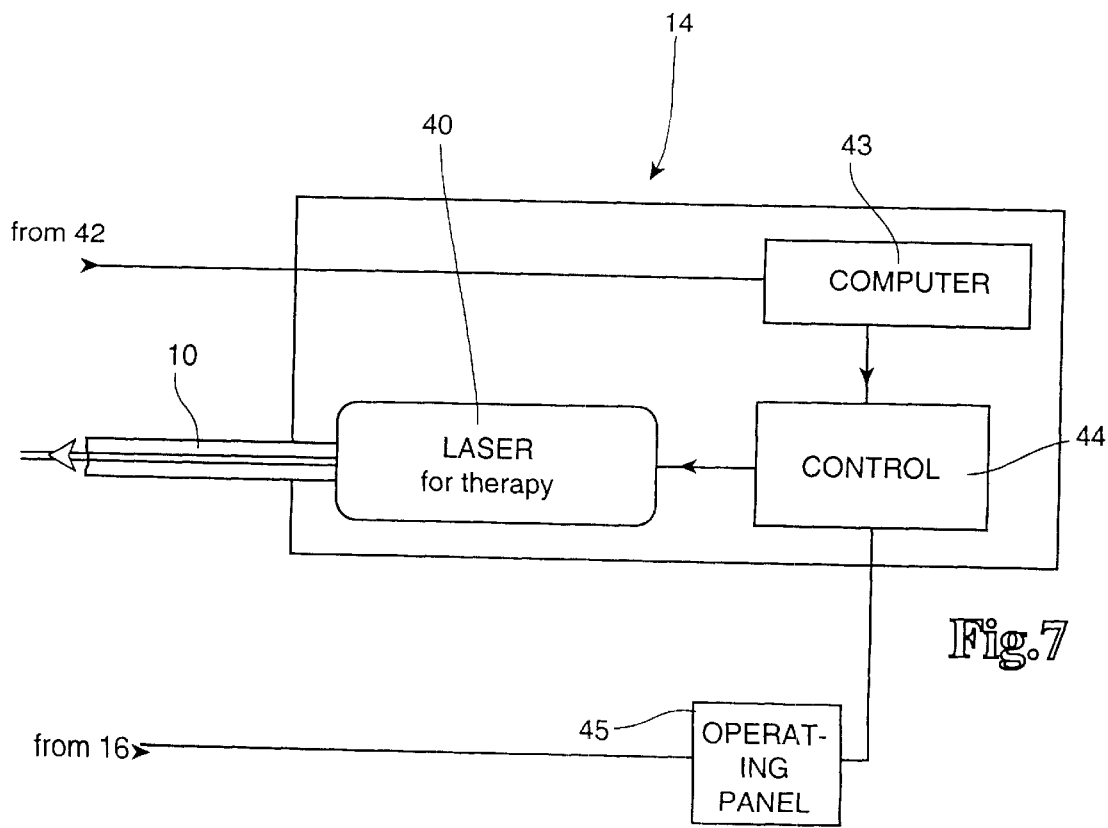
FIG. 7 a central unit to be used in connection with the handpiece shown in FIG. 6.

FIG. 6 shows another embodiment of the treatment device. The handpiece shown in FIG. 6 has exactly the same design as the handpiece described by means of FIG. 2, so that it is unnecessary to repeat these parts. However, the handpiece shown in FIG. 6 additionally comprises a sensor 42 which is equipped with an optical lens 43. The sensor and the optical lens are positioned so that an image of the blood vessel treated by the laser beam is formed on the light-sensitive surface of the sensor 42, and the sensor 42 is thus able to measure the reflected proportion of the light. The light power measured by the sensor 42 is transmitted via an electrical lead (not shown) to the central unit 14 (see FIG. 7). There it is processed in the computer 43 in the manner already described by means of FIGS. 1 to 5, and is transmitted to the control unit 44 which causes the laser 40 to trigger appropriate light pulses for the laser therapy if the trigger switch 16 is actuated.

What is claimed is:

1. A device for treating growing, dilated or malformed blood vessels with a laser emitting a laser beam in a wavelength range from 750 mn to 850 nm and a specific power, the device comprising a measuring unit measuring the concentration of an exogenous chromophore, introduced into the blood stream, which absorbs the laser beam in the blood vessel to be treated, and a control unit controlling the power of the laser beam in a contrary sense to the measured concentration.

2. The device as claimed in claim 1, wherein the measuring unit is a reflection measuring unit.

3. The device as claimed in claim 1, wherein, for measuring the concentration of the chromophore, the control unit causes the laser to emit a pilot laser pulse having a power which is so small that it causes no permanent changes in the blood vessel or the tissue surrounding the latter.

4. The device as claimed in claim 3, wherein the measuring unit comprises a computing unit which determines the chromophore concentration from the power of the pilot laser pulse and a reflected fraction thereof.

5. The device as claimed in claim 1, wherein the measuring unit has its own measuring light source.

6. The device as claimed in claim 1, wherein the control unit controls the power of the laser beam in inverse proportion to the chromophore concentration found.

7. The device as claimed in claim 1, wherein the laser generates the laser beam in the form of pulses.

8. The device as claimed in claim 7, wherein the pulses have a substantially rectangular shape.

9. The device as claimed in claim 7, wherein the pulses have a duration of less than 10 ms, preferably from 1 to 5 ms.

10. The device as claimed in claim 7, wherein the pulses can be executed singly.

11. The device as claimed in claim 7, wherein the pulses can be executed as double pulses with a pause of less than 5 ms.

12. The device as claimed in claim 7, wherein the control unit controls the pulse length in a contrary sense to the power.

13. The device as claimed in claim 1, wherein the laser is a diode laser.

14. The device as claimed in claim 1, wherein the laser has a power of from 100 to 800 W.

15. The device as claimed in claim 1, wherein the laser emits light with a wavelength of 805 nm.

16. The device as claimed in claim 1, wherein the laser is connected via a light guide to a handpiece.

17. The device as claimed in claim 16, wherein the handpiece has a transparent contact area for contact with a patient's skin.

18. The device as claimed in claim 16, wherein the handpiece has a housing with an illumination unit.

19. The device as claimed in claim 16, wherein the handpiece has a magnifier and a scale for measuring the vessels to be treated.

20. The device as claimed in claim 16, wherein the handpiece has a spectrally selective mirror for feeding in the laser beam.

21. The device as claimed in claim 20, wherein the mirror is a dichroic mirror.

22. The device as claimed in claim 16, wherein the handpiece has an aiming mark.

23. The device as claimed in claim 16, wherein the handpiece has an adjustable aperture for limiting the diameter of the laser beam.

24. The device as claimed in claim 16, wherein the handpiece has a cooling unit.

25. The device as claimed in claim 16, wherein the handpiece is connected to a video camera.

26. The device as claimed in claim 25, wherein the video camera is coupled to a monitor.

27. The device as claimed in claim 26, wherein the monitor provides a false color display of the chromophore concentration.

28. The device as claimed in claim 1, wherein the control unit blocks emission of laser light by the laser when the chromophore concentration found by the measuring unit is below a preset lower threshold.

29. The device as claimed in claim 1, wherein the control unit blocks emission of light pulses by the laser when the chromophore concentration found by the measuring unit is above a preset upper threshold.

30. The device as claimed in claim 1, comprising an intensity sensor to which part of a light reflected by the patient's blood vessel is passed.

31. The device as claimed in claim 30, wherein the intensity sensor is arranged in the handpiece.

32. The device as claimed in claim 30, comprising an outcoupling mirror which passes reflected light to the intensity sensor.

33. The method as claimed in claim 1, wherein the biological material is a human patient to whom the chromophore is administered intravenously.

34. The method as claimed in claim 33, wherein the light beam is directed onto the skin of said patient.

35. A method for treating biological material with a light beam having a wavelength in the range of 750 nm to 850 nm, the method comprising the steps of:

a) introducing into the biological material a chromophore which absorbs light in the range of 750 nm to 850 nm, b) directing a probe light beam having a wavelength in the range of 750 nm to 850 nm onto said biological material, a fraction of said probe light beam being reflected by said biological material, c) measuring the intensity of said reflected fraction of said probe light beam, d) directing said light beam onto said biological material and controlling its power in accordance with the measured intensity of said reflected fraction of said probe light beam.

36. The method as claimed in claim 35, wherein indocyanine green is used as the chromophore.

37. A device for treating growing, dilated or malformed blood vessels with a laser, the device comprising a measuring unit measuring the concentration of an exogenous chromophore, introduced into the blood stream, which absorbs the laser beam in the blood vessel to be treated, and a control unit controlling the power of the laser beam in a contrary sense to the measured concentration.

38. A method for treating biological material with a laser beam, the method comprising the steps of:

introducing into the biological material a chromophore which absorbs the laser beam;

directing a probe light beam onto said biological material, a fraction of said probe light beam being reflected by said biological material;

measuring the intensity of said reflected fraction of said probe light beam; and directing said light beam onto said biological material and controlling its power in accordance with the measured intensity of said reflected fraction of said probe light beam.

39. A device for treating growing, dilated or malformed blood vessels with a laser, the device comprising:

a measuring unit measuring the concentration of an exogenous chromophore, introduced into the blood stream, which absorbs the laser beam in the blood vessel to be treated; and a control unit controlling the power of the laser beam in an inverse proportion to the measured concentration of the exogenous chromophore.

40. A device for treating growing, dilated or malformed blood vessels with a laser, the device comprising:

a measuring unit measuring the concentration of an exogenous chromophore which absorbs the laser beam in the blood vessel to be treated; and a control unit controlling the power of the laser beam in a contrary sense to the measured concentration, wherein the monitor provides a false color display of the chromophore concentration.

* * * * *